US010471227B1

(12) United States Patent
Morris

(10) Patent No.: US 10,471,227 B1
(45) Date of Patent: Nov. 12, 2019

(54) LOW FLOW ADAPTOR TO DELIVER AEROSOLS VIA NASAL CANNULA WITHOUT CRASHOUT

(71) Applicant: Martin Allan Morris, Monticello, IL (US)

(72) Inventor: Martin Allan Morris, Monticello, IL (US)

(*) Notice: Subject to any disclaimer, the term of this patent is extended or adjusted under 35 U.S.C. 154(b) by 0 days.

(21) Appl. No.: 16/106,815

(22) Filed: Aug. 21, 2018

Related U.S. Application Data

(63) Continuation of application No. 16/032,907, filed on Jul. 11, 2018.

(51) Int. Cl.
| | | |
|---|---|---|
| *A61M 16/08* | (2006.01) | |
| *A61M 11/00* | (2006.01) | |
| *A61M 15/00* | (2006.01) | |
| *A61M 16/06* | (2006.01) | |
| *A61M 16/16* | (2006.01) | |

(52) U.S. Cl.
CPC ...... *A61M 16/0833* (2014.02); *A61M 11/002* (2014.02); *A61M 15/0085* (2013.01); *A61M 16/0672* (2014.02); *A61M 16/0875* (2013.01); *A61M 11/005* (2013.01); *A61M 16/16* (2013.01); *A61M 2202/064* (2013.01)

(58) Field of Classification Search
CPC .. A61M 11/00; A61M 11/001; A61M 11/002; A61M 11/003; A61M 11/005; A61M 15/0001; A61M 15/002; A61M 15/0085; A61M 15/08; A61M 16/00; A61M 16/0672; A61M 16/08; A61M 16/0808; A61M 16/0816; A61M 16/0833; A61M 16/0875; A61M 16/14; A61M 16/147; A61M 16/16; A61M 2202/064; A61M 39/00; A61M 39/10; A61M 2039/1027; A61M 2202/02; A61M 2202/0241; A61M 2207/00; A61M 2207/10; A61M 2210/06; A61M 2210/0618; A61M 2240/00; B65D 83/14–759

See application file for complete search history.

(56) References Cited

U.S. PATENT DOCUMENTS

| | | | |
|---|---|---|---|
| 5,355,872 A | 10/1994 | Riggs et al. | |
| 8,418,690 B2 | 4/2013 | Power et al. | |
| 9,572,950 B2 | 2/2017 | Power et al. | |
| 2001/0050080 A1* | 12/2001 | Seakins | A61M 16/08 128/203.16 |

(Continued)

FOREIGN PATENT DOCUMENTS

WO   2008116165 A2   3/2008

OTHER PUBLICATIONS

Aerogen Solo, www.aerogen.com/aerogen-solo-3/, as printed Jul. 10, 2018, 5 pages.

(Continued)

*Primary Examiner* — Timothy A Stanis
*Assistant Examiner* — Matthew D Ziegler
(74) *Attorney, Agent, or Firm* — D'Hue Law LLC; Cedric A. D'Hue

(57) ABSTRACT

A housing and method of using the same is configured and coupled to an aerosol generator which delivers aerosol into an oxygen stream transporting both to a patient via a nasal cannula, in a way to minimize condensation at low liters per minute flow rate.

17 Claims, 6 Drawing Sheets

(56) References Cited

U.S. PATENT DOCUMENTS

| | | | |
|---|---|---|---|
| 2002/0100320 A1* | 8/2002 | Smith | A61M 16/1075 |
| | | | 73/431 |
| 2002/0100478 A1* | 8/2002 | Prime | A61M 16/208 |
| | | | 128/205.24 |
| 2004/0261797 A1* | 12/2004 | White | A61M 16/0666 |
| | | | 128/206.11 |
| 2006/0120968 A1 | 6/2006 | Niven et al. | |
| 2007/0083677 A1 | 4/2007 | Cecka et al. | |
| 2007/0267010 A1 | 11/2007 | Fink et al. | |
| 2010/0012127 A1* | 1/2010 | Roth | A61M 16/0808 |
| | | | 128/205.29 |
| 2010/0065053 A1* | 3/2010 | Haveri | A61M 16/042 |
| | | | 128/204.18 |
| 2010/0071693 A1* | 3/2010 | Allum | A61M 16/04 |
| | | | 128/203.27 |
| 2011/0011395 A1 | 1/2011 | Mazela et al. | |
| 2011/0230820 A1* | 9/2011 | Lillis | A61M 11/005 |
| | | | 604/24 |
| 2017/0182279 A1 | 6/2017 | Power et al. | |
| 2017/0304565 A1 | 10/2017 | Allosery et al. | |
| 2018/0001045 A1* | 1/2018 | Cortez, Jr. | A61M 16/0069 |
| 2018/0021530 A1 | 1/2018 | Fink et al. | |
| 2018/0104424 A1 | 4/2018 | Akouka et al. | |
| 2018/0333555 A1* | 11/2018 | Burke | A61M 16/106 |
| 2019/0070400 A1* | 3/2019 | Chelak | A61M 39/045 |

OTHER PUBLICATIONS

Neotech Ram Cannula, www.neotechproducts.com/product/neotech-ram-cannula/#, as printed Jul. 10, 2018, 8 pages.

* cited by examiner

LOW FLOW ADAPTOR TO DELIVER AEROSOLS VIA NASAL CANNULA WITHOUT CRASHOUT

CROSS-REFERENCE TO RELATED APPLICATIONS

This application is a continuation of U.S. patent application Ser. No. 16/032,907, filed on Jul. 11, 2018, which is incorporated by reference in its entirety.

FIELD

One or more embodiments of the present invention relates to adapters for introducing aerosols into a patient in need of such introduction, and more particularly to adapters for nebulizers for introducing aerosols into nasal cannulas with low and laminar flow without crashout into a patient in need of such introduction.

SEQUENCE LISTING

A computer program listing the adaptor of the present disclosure is submitted as a sequence listing and expressly incorporated by reference.

BACKGROUND

The need for effective therapeutic treatment of patients has resulted in the development of a variety of pharmaceutical formulation delivery techniques. One traditional technique involves the oral delivery of a pharmaceutical formulation in the form of a pill, capsule, elixir, or the like. However, oral delivery can in some cases be undesirable. For example, many pharmaceutical formulations may be degraded in the digestive tract before the body can effectively absorb them.

In such inhalation techniques, aerosol is added to the inspiratory gas by placing a T-piece or equivalent in the circuit and entraining the aerosol with the inspiratory gas. In such arrangements the aerosolization device is downstream of the gas source and upstream of the patient. Inhalable drug delivery, also known as pulmonary delivery, where a patient orally or nasally inhales an aerosolized pharmaceutical formulation to deliver the formulation to the patient's respiratory tract, may also be effective and/or desirable. In some inhalation techniques, an aerosolized pharmaceutical formulation provides local therapeutic treatment and/or prophylaxis to a portion of the respiratory tract, such as the lungs, to treat respiratory diseases such as asthma and emphysema and/or to treat local lung infections, such as fungal infections and cystic fibrosis. In other inhalation techniques, a pharmaceutical formulation is delivered deep within a patient's lungs where it may be absorbed into the bloodstream for systemic delivery of the formulation throughout the body.

Many types of aerosolization devices exist including devices comprising a pharmaceutical formulation stored in or with a propellant, devices that aerosolize a dry powder, devices which use a compressed gas or other mechanism to aerosolize a liquid pharmaceutical formulation, and similar devices.

One known aerosolization device is commonly referred to as a nebulizer. A nebulizer comprises a container having a reservoir that contains a fluid, liquid, or liquefiable formulation. If liquid, the pharmaceutical formulation generally comprises an active agent that is either in solution or suspended or dispersed within a liquid medium. Various medicaments available in liquid form may be aerosolized for use in therapies. Any suitable medicament, therapeutic agent, active substance or pharmaceutically active compound than can be nebulized may be employed. It can also act to deliver any agent presented in an aqueous drug solution. Where the liquid being aerosolized is water, saline or other solution of water or saline, the aerosol generator also provides additional humidity to the circuit which may enhance patient comfort where no other humidity source is present.

Energy is introduced into the reservoir to aerosolize the liquid pharmaceutical formulation to allow delivery to the lungs of a patient. In one type of nebulizer, generally referred to as a jet nebulizer, compressed gas is forced through an orifice in the container. The compressed gas forces liquid to be withdrawn through a nozzle, and the withdrawn liquid mixes with the flowing gas to form aerosol droplets. A cloud of droplets is then administered to the patient's respiratory tract. In another type of nebulizer, generally referred to as a vibrating mesh nebulizer, energy such as high frequency ultrasonic waves are generated to vibrate a mesh. This vibration of the mesh aerosolizes the liquid pharmaceutical formulation to create an aerosol cloud that is administered to the patient's lungs. Vibrating mesh technology generates an aerosol with a precisely controlled particle size range optimized in general respiratory use for deep lung deposition. The distribution of particles can be represented as a normal distribution with the majority of particles produced in the range 2-10 microns. Such technology is described in detail in U.S. Pat. No. 8,418,690, Col. 9, lines 8-48, the subject matter of which is expressly incorporated by reference. Furthermore, functions such as control of the nebulizer are described in detail in U.S. Pat. No. 8,418,690, Col. 9, line 58—Col. 11, line 38, the subject matter of which is expressly incorporated by reference.

In still another type of nebulizer, ultrasonic waves are generated to directly vibrate and aerosolize the pharmaceutical formulation.

The valves, devices, fittings, systems, components and adapters for introducing aerosols into a patient in need of such introduction may also be suitably used with dry powder administration devices, such as passive dry powder inhalers and active dry powder inhalers. A passive dry powder inhaler comprises an inhalation device which relies upon a patient's inspiratory effort to disperse and aerosolize a pharmaceutical composition contained within the device in a reservoir or in a unit dose form and does not include inhaler devices which comprise a means for providing energy, such as pressurized gas and vibrating or rotating elements, to disperse and aerosolize the drug composition. An active dry powder inhaler comprises to an inhalation device that does not rely solely on a patient's inspiratory effort to disperse and aerosolize a pharmaceutical composition contained within the device in a reservoir or in a unit dose form and does include inhaler devices that comprise a means for providing energy to disperse and aerosolize the drug composition, such as pressurized gas and vibrating or rotating elements.

Nebulizers are often used to deliver (1) an aerosolized pharmaceutical formulation to a hospitalized or non-ambulatory patient; and/or (2) large doses of aerosolized active agent; and/or (3) an aerosolized pharmaceutical formulation to a child or other patient unable to receive a dry powder or propellant based pharmaceutical formulation.

Nebulizers are useful for delivering an aerosolized pharmaceutical formulation to the respiratory tract of a patient who is breathing via a nasal cannula. But there are problems associated with the introduction of aerosolized pharmaceutical formulation via nasal cannulas. For example, crashout of the pharmaceutical formulations onto the interior of the apparatus decreases the efficacy of the treatment.

US patent publication no. US20060120968A1 teaches crashout reduces the quantities of the aerosolized material reaching the lungs because of inefficient delivery to the lungs. A significant contributor to extrathoracic losses is material deposited at or around the nasal prongs or nasal cannula where there is potential to clog the prongs during extended treatments.

Devices in the prior art require filters to prevent crashout, but the efficacy of the treatment is reduced. International PCT patent application publication no. WO2008116165A2, by Lemahieu et al., disclose methods and systems of delivering medication via inhalation. The system utilizes a particle filter to limit particle deposition, aka crashout, on the walls of the mask and any air hose used with the device. US patent application publication no. US20070267010A1, by Fink et al., discloses an inspiratory filter that removes aerosolized droplets.

Devices in the prior art minimize corners and shorten the delivery system in an effort to prevent efficacy reduction due to crashout. US patent application publication no. US20110011395A1, by Mazela et al., discloses a device with an aerosol flow channel formed into a funnel-like shape that minimizes corners, and thus helps to prevent the accumulation of deposits within the adaptor. The '395 published patent application also teaches preferably, the aerosol tube is expandable to secure the optimized placement of the nebulizer, for example, as close to the patient as possible but in comfortable location to avoid restriction of any nursing procedures and allow patient for some head motion. Expandable tubes help avoid creation of sharp angles and thus avoid potential aerosol deposition, aka crashout, within the delivery system.

US patent application publication no. US20070083677A1, by Cecka et al., discloses devices, including adapters, for endobronchial therapy that include nasal delivery, cannulas, and delivery of aerosols. The '677 teaches nasal administration of an aerosol at an air flow rate of 60 L/min and is silent regarding crashout.

US patent application no. US20170304565A1, titled "Inhalation device for use in aerosol therapy of respiratory diseases", by Koen Allosery et al., discloses an inhalation device for use in aerosol therapy of respiratory diseases. The device comprises a face mask with a vibrating mesh nebulizer and a valve insertable in the flow channel of the suction device through the lateral openings. The flow channel facilitates low and laminar flow through the device.

The device can be connected to a gas source via an opening in the flow channel, and results in a lower flow. The flow channel extends from the gas inlet opening to the aerosol inlet opening of the face mask. The flow channel facilitates a certain flow resistance of an aerosol flow rate of 1 to 20 L/min in between the gas inlet opening and the inlet opening of the face mask. The upstream portion of the flow channel comprises the portion from the gas inlet opening (and including) the nebulizer, the segment to the lateral opening that allows 1 to 20 L/min constant flow rate, and in particular, from about 1 L/min to about 5 L/min. The flow channel size and shape are configured to achieve a laminar flow of gas conducted through the flow channel at a constant flow rate.

Regarding the flow channel, the '565 published patent application also teaches a sudden change in diameter has to be avoided, and it is preferred than the inner wall is formed of a material having a smooth inner wall surface. An example of suitable upstream segment is a regular cylindrical pipe formed of an inert polymeric material having a polished stainless steel or a smooth surface. The '565 published patent application also teaches the gas inlet opening is formed of a tube fitting, to facilitate attachment of a gas source, substantially such as stainless steel, and to allow laminar flow of inert gas. The gas inlet opening is also formed of a smooth material. For example, it is more advantageous to use a tube fitting having a shaped inner wall that is smooth and cylindrical in order facilitate laminar flow of gas.

The substantially laminar flow refers to a Reynold's number of about 2300 or less (Reynold's number). Preferably, the upstream segment of the flow channel has a size and shape to achieve a Reynolds number of not more than 2000 in 1 to 5 L/min flow rate. The '565 published patent application teaches, in particular, when the gas flow rate is 1 to 5 L/min at the gas inlet, it allows the creation of a slight over-pressure in the face mask. The over-pressure facilitates inhalation by the patient of the aerosol spray generated by the device. The over pressure allows for a normal breathing pattern, substantially without interference, and effective drug delivery.

Regarding laminar flow, US patent application publication no. US20180104424A1, titled "Inhaler and Methods of Use Thereof", by Henri Akouka et al., discloses a medicament delivery device comprises a dosing chamber configured to contain dry powder medicament and a channeling means to conduit air flow. The '424 published patent application teaches that a consistent cross-sectional area throughout the upper flow path may promote a laminar air flow through the upper flow path. Alternatively, the cross-sectional area of the upper flow path may vary along its length, but laminar air flow is still promoted as long as a minimum cross-sectional area is met, for example, at least about 40 mm$^2$, at least about 50 mm$^2$ or at least about 60 mm$^2$. Furthermore, the '424 published patent application discloses that the exit channel and dosing chamber are aligned to promote a laminar flow of the aerosolized pharmaceutical out of the dosing chamber and through the exit channel.

US published patent application no. US20180021530A1, by Fink et al., discloses the aerosolization device may include a conduit, an aerosol generator, a restrictor disposed within the conduit, and an indicator mechanism. The restrictor defines a plurality of apertures disposed along an outer periphery of the restrictor configured to provide a relatively laminar flow downstream of the restrictor compared to upstream of the restrictor. The '530 published patent application teaches that laminar flow provides a consistent velocity field to deliver the aerosolized particles to the user's respiratory system in a consistent manner while minimizing impactive losses; additionally, the laminar flow minimizes an amount of aerosolized medicament that may be deposited on a wall of the conduit. The exemplary embodiments in the '530 published patent application teach flow rates between 5 and 14 L/min, but the '530 is silent regarding low flow.

U.S. Pat. No. 5,355,872 A, by Riggs et al., discloses a low flow rate nebulizer apparatus and method of nebulization. A nebulizer device, comprising: (a) a housing defining an interior volume, including a reservoir portion for holding medicament for entrainment into a carrier gas to form a delivery gas mixture comprising nebulized medicament and carrier gas; (b) a discharge port connected to the housing in flow communication with the interior volume, for discharging the delivery gas mixture from the housing; (c) a jet passage member having (i) an inlet portion for introduction of carrier gas and (ii) a nozzle portion positioned in the interior volume of the housing for discharging carrier gas in jet form in the interior volume, for entrainment of medicament from the reservoir portion of the housing in the carrier gas jet, such nozzle portion comprising a nozzle orifice accommodating carrier gas flow, wherein the nozzle orifice has an equivalent orifice diameter in the range of from about 0.005 inch to about 0.020 inch. The '872 patent teaches a low flow rate nebulization method comprising flowing the carrier gas through the jet passage member in the range of from about 0.5 to about 3.25 liters per minute, to disperse the medicant into the carrier gas and form a pulmonarily effective nebulized medicant in the carrier gas, as a medicant/carrier gas mixture. At flow rate values below about 0.5 liters per minute, the volumetric flow rate of carrier gas tends to become insufficient to achieve good dispersion of the medicant in the flowing gas stream. At volumetric flow rate values above about 3.25 liters per minute, the small-size orifice dimensions employed in the practice of the invention tend to produce a back pressure which renders it disproportionately more difficult to achieve a reliable coupling and seal between the inlet portion of the jet passage member and the associated carrier gas flow means.

U.S. Pat. Nos. 8,418,690 and 9,572,950, and U.S. published patent application number 2017/0182279 by Power et al., disclose a supplemental oxygen delivery system which aerosol generator 9 delivers aerosol into an oxygen stream 13 flowing between an inlet 14 and an outlet 15 of the housing 10 or 30 which sits in the circuit from the supplemental oxygen supply to a patient via a nasal cannula 3 or a face mask 4. Housing 10 is designed to selectively allow only smaller aerosol particle sizes (less than 3 microns), suitable for transport along narrow bore tubing, onto to the patient while encouraging localized deposition of the aerosol heavier particles. Housing 10 also has a removable plug 16 in the base 17 thereof for draining any liquid that accumulates in the housing 10. As illustrated in FIG. 19 and Example starting in Col. 6, line 32, more than fifty percent of the aerosol particles, specifically the particles larger than the Volumetric Mean Diameter (VMD or Dv50) are removed from the distribution and are drained as liquid from housing 10.

There remains a need for more effective adapters for introducing aerosols at low flow into nasal cannulas without crashout. Accordingly, there also remains a need for improved methods of treatment and/or prevention that use such adapters.

SUMMARY

In one aspect of the invention, a device for delivery of aerosol along with supplemental oxygen from an oxygen supply to the nasal cannula of a patient is disclosed, wherein the device comprises a housing, wherein the housing includes a base and a cylindrical wall, wherein the base and the cylindrical wall define a chamber through which supplemental oxygen is led, and two couplers, wherein the first of the two couplers is an inlet for supplemental oxygen supply into the chamber, wherein the second of the two couplers is an outlet for delivery of the supplemental oxygen supply containing an aerosol, wherein each of the two couplers is configured to engage a nasal cannula line, wherein chamber wall is configured to snugly fit to an aerosol delivery portion of a nebulizer, wherein the aerosol delivery portion of nebulizer is not positioned to act as a baffle to air flow between the two couplers, wherein there is no baffle or impediment to air flow and aerosol through adaptor, wherein the housing and couplers are designed to facilitate laminar flow.

In a further aspect of the disclosure, a computer readable medium storing computer readable instructions which, when acted upon by a 3D printer, cause the 3D printer to print an adaptor comprising a housing, wherein the housing includes a base and a cylindrical wall, wherein the base and the cylindrical wall define a chamber through which supplemental oxygen is led, and two couplers, wherein the first of the two couplers is an inlet for supplemental oxygen supply into the chamber, wherein the second of the two couplers is an outlet for delivery of the supplemental oxygen supply containing an aerosol, wherein each of the two couplers is configured to engage a nasal cannula line, wherein chamber wall is configured to snugly fit to an aerosol delivery portion of a nebulizer, wherein the aerosol delivery portion of nebulizer is not positioned to act as a baffle to air flow between the two couplers, wherein there is no baffle or impediment to air flow and aerosol through adaptor, wherein the housing and couplers are designed to facilitate laminar flow.

BRIEF DESCRIPTION OF THE DRAWINGS

The above-mentioned and other features of this disclosure, and the manner of attaining them, will become more apparent and the disclosure itself will be better understood by reference to the following description of embodiments of the disclosure taken in conjunction with the accompanying drawings, wherein.

Figure 1:
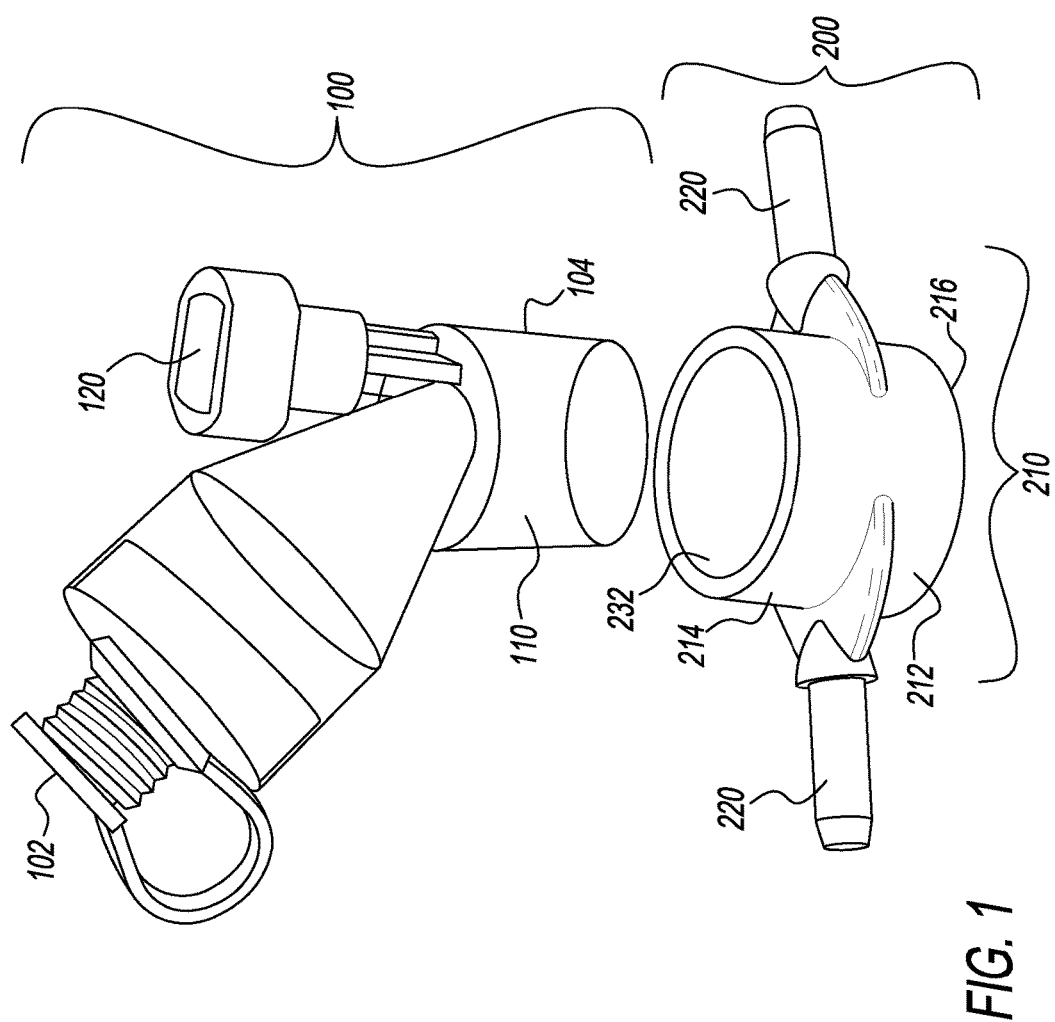
FIG. 1 illustrates an exploded view of the adaptor and nebulizer.

Corresponding reference characters indicate corresponding parts throughout the several views. Although the drawings represent embodiments of the present disclosure, the drawings are not necessarily to scale and certain features may be exaggerated in order to better illustrate and explain the present disclosure.

DETAILED DESCRIPTION OF THE EXEMPLARY EMBODIMENTS

The embodiments disclosed below are not intended to be exhaustive or limit the disclosure to the precise forms disclosed in the following detailed description. Rather, the embodiments are chosen and described so that others skilled in the art may utilize their teachings.

Unless otherwise stated, a reference to a compound or component includes the compound or component by itself, as well as in combination with other compounds or components, such as mixtures of compounds.

As used herein, the singular forms "a", "an" and "the" include the plural reference unless the context clearly dictates otherwise.

All publications, patents and patent applications cited herein, whether supra or infra, are hereby incorporated by reference in their entirety to the same extent as if each individual publication, patent or patent application was specifically and individually indicated to be incorporated by reference.

"Crashout" is deposition of the compositions that are nebulized on the interior of the adaptor, tubing, and nasal cannula. Crashout reduces the concentration of the nebulized compositions delivered to the patient during treatment.

"Low flow" is a qualitative term to describes flow rates of about 1 L/min to 6 L/min, or alternatively anything less than 6 L/min.

Nebulizer 100 and adaptor 200 are illustrated in FIG. 1. Nebulizer 100 may be a vibrating mesh nebulizer sold by Aerogen (Chicago, Ill.) as Aerogen Solo (available online at www.aerogen.com/aerogen-solo-3/). Nebulizer 100 includes reservoir 102 which is capable of receiving a continuous feed and/or holding powder, fluid, liquid, or liquefiable formulation, the vibrating mesh 104, power cable receiver 120 to receive electrical power to drive the vibrating mesh 104, and the aerosol delivery portion 110.

Adaptor 200 comprises housing 210 and two couplers 220. Housing 210 includes base 212 and cylindrical wall 214. All parts of adaptor 200 including housing 210, base 212, cylindrical wall 214, and couplers 220 may be integrally formed using a 3D printer. Base 212 includes surface 216 so that adaptor 200 can be placed on a suitable surface, such as placing adaptor 200 horizontally on a flat surface like a table. Cylindrical wall 214 also defines opening 232 to accommodate aerosol delivery portion 110 of nebulizer 100. Opening 232 may be modified to accommodate other means to deliver aerosol or nebulized medicaments. In alternative embodiments, the means to deliver aerosol or nebulized medicament 300 may be a dry powder delivery device, or an aerosol delivery line from a compressor.

Figure 2:
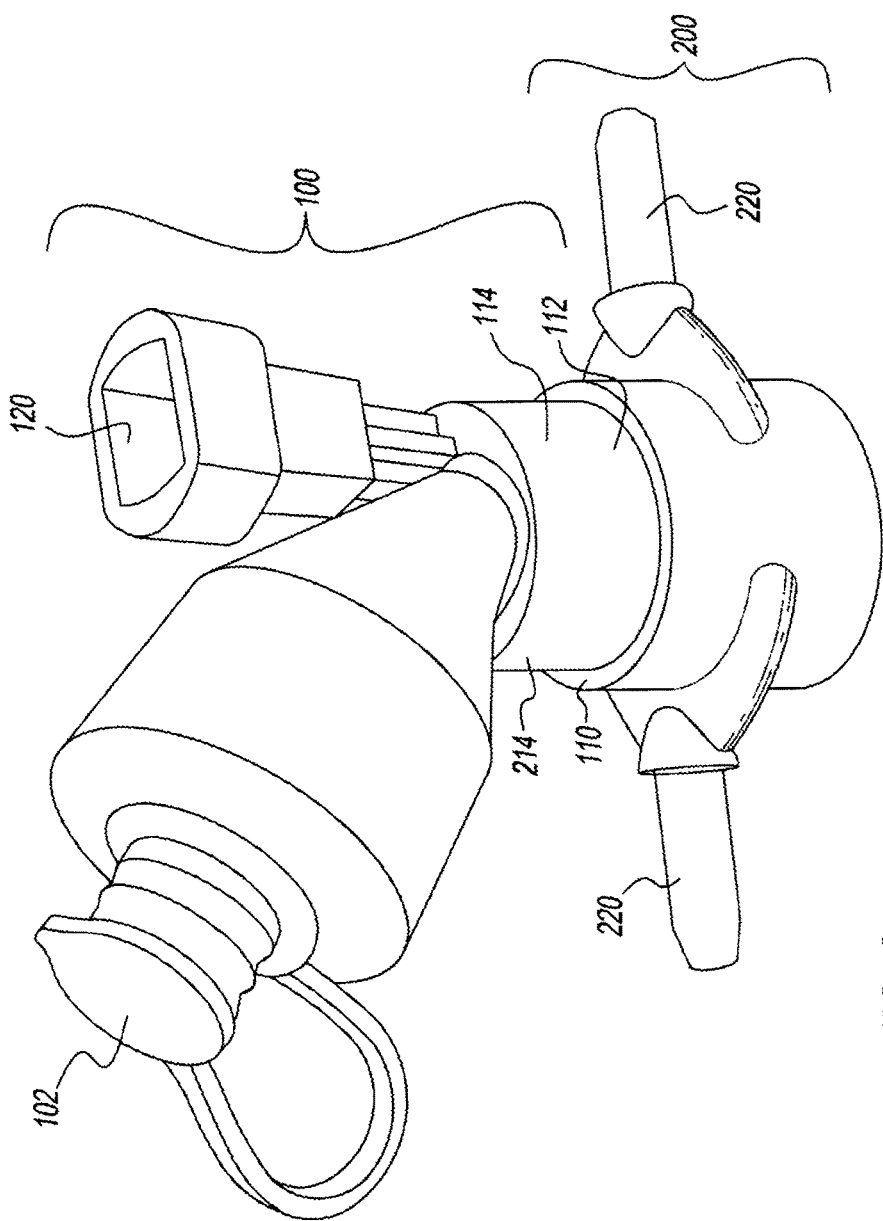
FIG. 2 illustrates a perspective view of the adaptor and nebulizer.
Figure 3:
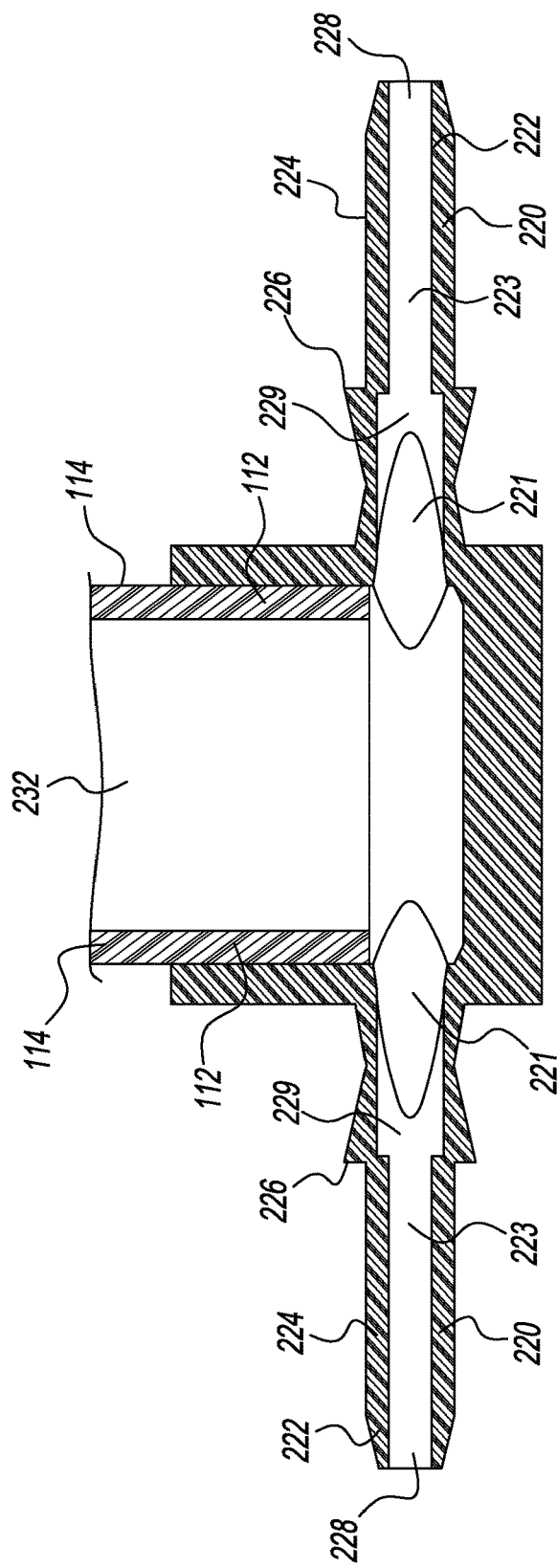
FIG. 3 illustrates a cross sectional side view of the adaptor cutting through both couplers.
Figure 4:
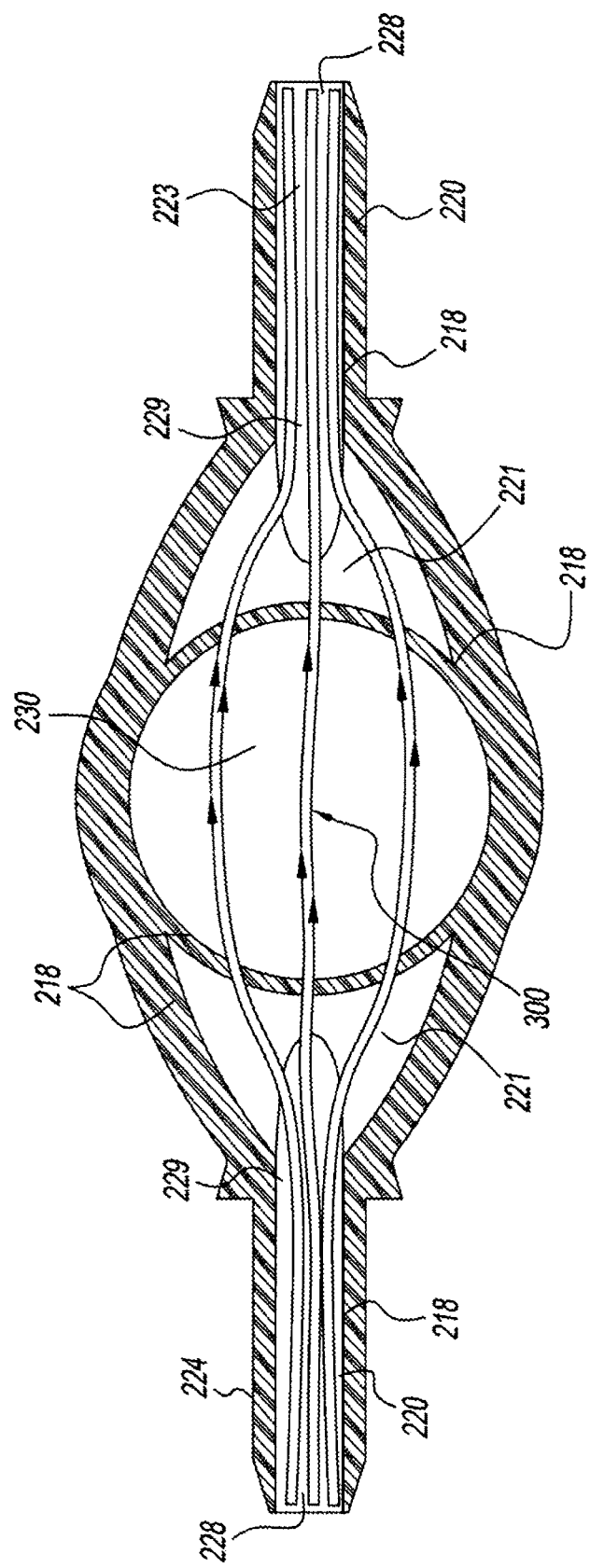
FIG. 4 illustrates cross sectional top view of the adaptor cutting through both couplers.
Figure 5:
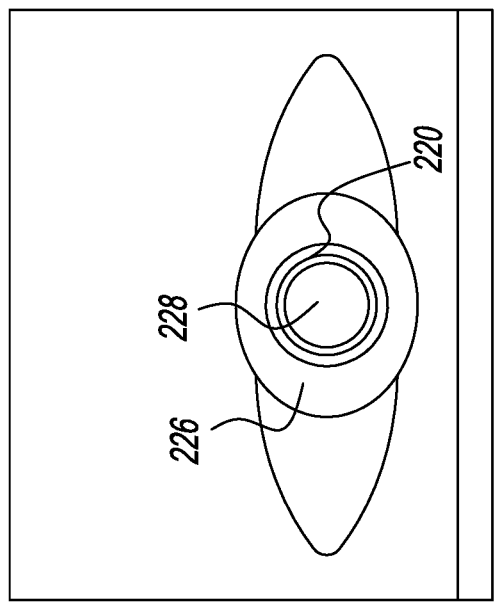
FIG. 5 illustrates an end view of the adaptor looking through both couplers.
Figure 6:
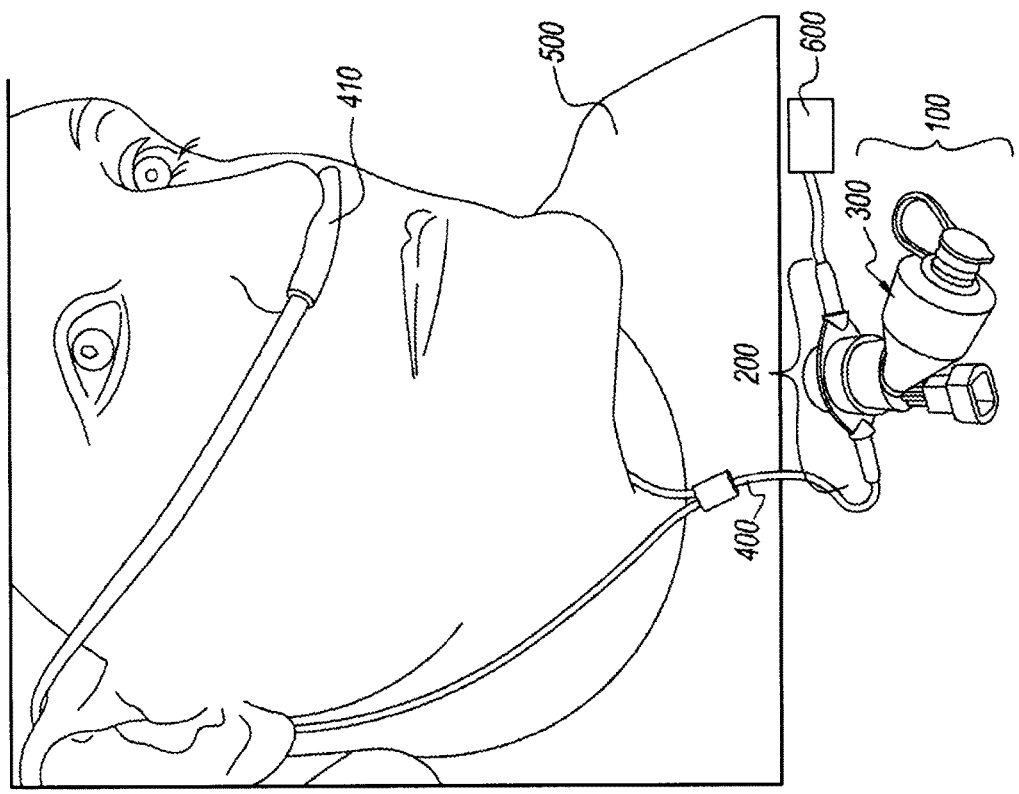
FIG. 6 illustrates a perspective view of the adaptor coupled to cannula lines going to the nose of a patient.

As best illustrated in FIG. 2 by one embodiment of the present disclosure, aerosol delivery portion 110 of nebulizer 100 is inserted into opening 232 of adaptor 200. Cylindrical wall 214 is configured to snugly fit to aerosol delivery portion 110 of nebulizer 100. Specifically, the aerosol delivery portion 110 may comprise collar 112 or neck 114 to facilitate mounting of the unit into opening 232 of adaptor 200. The interfitting may be a push fit with a portion of collar 112 located within opening 232 and a portion of neck 114 located outside of opening 232. This enables the unit of nebulizer 100 and adaptor 200 to be easily mounted and de-mounted, for example for cleaning. The neck 114 or collar 112 at least partially lines opening 232 of adaptor 200. Aerosol delivery portion 110 of nebulizer 100 is not positioned low enough in opening 232 to act as a baffle to air flow between couplers 220. Adaptor 200 is designed to pass all air flow and aerosol to the nasal cannula and ultimately to the patient. There is no sharp change in flow direction created by the presence of aerosol delivery portion 110.

As best illustrated in FIG. 3, couplers 220 are horizontally opposed with no sharp change in flow direction. Couplers 220 are also positioned at substantially the same level (z-direction) relative to each other to further minimize flow disturbance. Couplers 220 can be interchangeably used as an inlet or as an outlet for air flow. Couplers 220 are designed to snugly fit within a nasal cannula line 400 (FIG. 6). Couplers 220 include tapered ends 222, cylindrical shape 224 and abutments 226 to facilitate mating with nasal cannula line 400. Couplers 220 may be modified, such as in length and girth, to accommodate multiple sizes and shapes of nasal cannula lines.

Couplers 220 each define conduits 228. Conduits 228 include a cylindrical portion 223 along the length of the portion of the coupler 220 configured to engage a nasal cannula line 400. Conduits 228 also include a slightly larger cylindrical portion 229 which starts at the abutment 226 and continues to the opening 232 of the cylindrical wall 214. Each coupler 220 also defines void 221 which is generally shaped as an end of an ellipsoid.

As illustrated in FIGS. 3 and 4, housing 210 (FIG. 1) defines chamber 230 which is fluidly connected to voids 221 and cylindrical portions 223 and 229. Cylindrical portions 223 and 229 and voids 221 are fluidly connected allowing for air flow to travel in one coupler 220, specifically through cylindrical portion 224, through larger cylindrical portion 229, through void 221 and through chamber 230 and then out of adaptor through the other void 221, through the other larger cylindrical portion 229, through the other cylindrical portion 223 and out to through the other coupler 220. The interior of housing 210 and base 212 defining chamber and the interior walls 218 of couplers 220 are smooth and rounded to facilitate laminar flow. Furthermore, integrally formed parts facilitate laminar flow. Adaptor 200 configuration and facilitation of laminar flow permits laminar egress of aerosol into the cannula line minimizing turbulent flow, eddies or small packets, each of which can lead to condensate (aka rain out or crash out) forming as liquid droplets in chamber 230.

As best illustrated in FIGS. 2, 3 and 5, conduits 228 in couplers 220 are continuous with chamber 230 (FIG. 4). Aerosol delivery portion 110 of nebulizer 100 is not positioned low enough in opening 232 to act as a baffle to air flow between couplers 220. There is no sharp change in flow direction created by the presence of aerosol delivery portion 110 as illustrated by the lack of a portion of aerosol delivery portion 110 blocking air flow through adaptor 200.

As illustrated in FIG. 6, in one embodiment of the present disclosure, adaptor 200 is fitted with nebulizer 100, and fitted to nasal cannula line 400. Nebulizer 100 includes medicament 300. The medicament 300 is nebulized into aerosol, then the aerosol is passed into the air flow from gas supply 600 through adaptor 200, and then into canula line 400 where it is delivered to patient 500 by nasal cannula 410.

Adaptor 200 facilitates delivery in aerosol form of, for example, bronchodilators, including β-agonists, muscarinic antagonists, epinephrine, surfactants; pain-relief medications including anesthetics; migraine therapies; anti-infectives; anti-inflammatories, steroids, including corticosteroids; chemotherapeutic agents; mucolytics; vasodilators; vaccines and hormones. In addition substances classified as anti-thrombogenic agents, anti-proliferative agents, monoclonal antibodies, anti-neoplastic agents, anti-mitotic agents, anti-sense agents, anti-microbial agents, nitric oxide donors, anti-coagulants, growth factors, translational promoter, inhibitors of heat shock proteins, biomolecules including proteins, polypeptides and proteins, oligonucleotides, oligoproteins, siRNA, anti-sense DNA and RNA, ribozymes, genes, viral vectors, plasmids, liposomes, angiogenic factors, hormones, nucleotides, amino acids, sugars, lipids, serine proteases, anti-adhesion agents including but not limited to hyaluronic acid, biodegradable barrier agents may also be suitable.

The medicament 300 may for example, comprise long-acting beta-adrenoceptor agonists such as salmeterol and formoterol or short-acting beta-adrenoceptor agonists such as albuterol.

The medicament 300 may be a long-acting muscarinic antagonists such as tiotropium (Spiriva) or short-acting muscarinic antagonists such as ipratropium (Atrovent).

Typical anti-infectives include antibiotics such as an aminoglycoside, a tetracycline, a fluoroquinolone; anti-microbials such as a cephalosporin; and anti-fungals. Examples of antibiotics include anti-gram-positive agents such as macrolides, e.g. erythromycin, clarithromycin, azithromycin, and glycopeptides, e.g. vancomycin and teicoplanin, as well as any other anti-gram-positive agent capable of being dissolved or suspended and employed as a suitable aerosol, e.g. oxazolidinone, quinupristin/dalfopristin, etc. Antibiotics useful as anti-gram-negative agents may include am inoglycosides, e.g. gentamicin, tobramycin, amikacin, streptomycin, netilmicin, quinolones, e.g. ciprofloxacin, ofloxacin, levofloxacin, tetracyclines, e.g. oxytetracycline, doxycycline, minocycline, and cotrimoxazole, as well as any other anti-gram-negative agents capable of being dissolved or suspended and employed as a suitable aerosol.

Anti-inflammatories may be of the steroidal such as budesonide or ciclesonide, non-steroidal, such as sodium cromoglycate or biological type.

Typical local anesthetics are, for example, Ropivacaine, Bupivacaine, levobupivacaine, and Lidocaine.

Chemotherapeutic agents may be alkylating agents, anti-metabolites, anthracyclines, plant alkaloids, topoisomerase inhibitors, nitrosoureas, mitotic inhibitors, monoclonal antibodies, tyrosine kinase inhibitors, hormone therapies including corticosteroids, cancer vaccines, anti-estrogens, aromatase inhibitors, anti-androgens, anti-angiogenic agents and other anti-tumor agents.

Surfactant medications (sometimes referred to herein as "surfactants") are protein-lipid compositions, e.g. phospholipids, that are produced naturally in the body and are essential to the lungs' ability to absorb oxygen. They facilitate respiration by continually modifying surface tension of the fluid normally present within the air sacs, or alveoli, that tube the inside of the lungs. In the absence of sufficient surfactant, these air sacs tend to collapse, and, as a result, the lungs do not absorb sufficient oxygen. Insufficient surfactant in the lungs results in a variety of respiratory illnesses in both animals and humans. Since most of these surfactant medications are animal-based, the current supply is limited, and although synthetic surfactants are available, their manufacture is both inexact and expensive. In addition, the surfactant medications are typically high in viscosity and are difficult to deliver to the patient's respiratory system. The increased efficiency of the adaptor of the present disclosure, and the smaller amount of medicament 300 required for a treatment according to the present disclosure, can be a substantial advantage when such scarce and expensive medicaments are employed. The combination of surfactant with other medicaments to improve distribution in the lung and body is also possible. Surfactants also possess the capacity to act as anti-adhesion agents.

An adaptor 200 of the present disclosure is tested to ensure the adaptor minimized condensate (aka rain out or crash out) forming as liquid droplets in chamber 230 at low flow rate. Table 1 discloses the amount of condensate collected in a horizontal housing 210 after 3 mL 0.9% nasal saline is nebulized into aerosol using an Aerogen ultrasonic nebulizer 100 coupled to adaptor 200 at ambient temperature of 68° F. Different sizes of nasal cannulas (NC) and liters per minute (LPM) flow rates are tested.

Table 1: amount of condensate collected in a horizontal housing 210 after 3 mL 0.9% nasal saline is nebulized into aerosol using an Aerogen ultrasonic nebulizer 100 coupled to adaptor 200 at ambient temperature of 68° F.:

| | 0.5 LPM | 1 LPM | 2 LPM | 3 LPM | 4 LPM | 5 LPM | 6 LPM |
|---|---|---|---|---|---|---|---|
| NEONATAL NC | 1.2 ml | 0.3 ml | 0 ml | 0 ml | 0 ml | 0 ml | 0 ml |
| RAM CANNULA ORANGE | 1 ml | 0.2 ml | 0 ml | 0 ml | 0 ml | 0 ml | 0 ml |
| RAM CANNULA BLUE | 1.1 ml | 0.3 ml | 0. ml | 0 ml | 0 ml | 0 ml | 0 ml |
| RAM CANNULA GREEN | 1.3 ml | 0.6 ml | 0.1 ml | 0 ml | 0 ml | 0 ml | 0 ml |
| RAM CANNULA WHITE | 1.3 ml | .6 ml | 0.1 ml | 0 ml | 0 ml | 0 ml | 0 ml |
| INFANT NC | 1.3 ml | 0.5 ml | 0.1 ml | 0 ml | 0 ml | 0 ml | 0 ml |
| PEDIATRIC NC | 1.3 ml | 0.7 ml | 0.2 ml | 0 ml | 0 ml | 0 ml | 0 ml |
| ADULT NC | 0.9 ml | 0.2 ml | 0 ml | 0 ml | 0 ml | 0 ml | 0 ml |

Ram Cannulas come in a variety of sizes and colors (Micro Preemie is White; Preemie is Green; Newborn is Blue; Infant is Orange) and are sold by Neotech (Valencia, Calif.) (available online at www.neotechproducts.com/product/neotech-ram-cannula/#).

Table 1 surprisingly shows that condensate is eliminated for some nasal cannulas at flow rates as low as 2 liters per minute. Table 1 also surprisingly shows that condensation rates are typically around 20% or lower at flow rates as low as 1 liter per minute. Table 1 also surprisingly shows that adaptor 200 did not result in a condensation rate as high as 50% even at 0.5 liters per minute flow rate.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

What is claimed is:

1. A device for delivery of aerosol along with supplemental oxygen from an oxygen supply to a nasal cannula of a patient, the device comprising:

a) a housing, wherein the housing includes a base and a cylindrical wall, wherein the base and the cylindrical wall define a chamber through which supplemental oxygen is configured to be led, and b) two couplers, wherein a first of the two couplers is an inlet for supplemental oxygen supply into the chamber, wherein a second of the two couplers is an outlet for delivery of the supplemental oxygen supply containing an aerosol, wherein each of the two couplers is configured to engage a nasal cannula line, wherein the cylindrical wall is configured to snugly fit to an aerosol delivery portion of a nebulizer, wherein the aerosol delivery portion of the nebulizer is not positioned to act as a baffle to air flow between the two couplers, wherein there is no baffle or impediment to air flow and aerosol through the device, wherein the housing and couplers are designed to facilitate laminar flow, wherein each of the two couplers also defines a void which is shaped as an end of an ellipsoid, and wherein the void extends outward and perpendicular from the cylindrical wall.

2. The device of claim 1 wherein the device including housing, base, cylindrical wall, and two couplers are integrally formed.

3. The device of claim 2 wherein the device is formed using a 3D printer.

4. The device of claim 1 wherein each of the two couplers defines a conduit which includes a cylindrical portion along a length of a portion of the coupler.

5. The device of claim 1 wherein each of the two couplers defines a slightly larger cylindrical portion which starts at an abutment of each coupler and continues to the chamber.

6. The device of claim 1 wherein each void starts in the slightly larger cylindrical portion and terminates in the chamber.

7. The device of claim 6 wherein the chamber is fluidly connected to the voids and all cylindrical portions.

8. The device of claim 1 wherein condensation of the aerosol is eliminated in the housing at 2 liters per minute flow rate.

9. The device of claim 1 wherein a condensation rate of the aerosol is 20% or lower in the housing at 1 liter per minute flow rate.

10. The device of claim 1 wherein a condensation rate of the aerosol is 10% or lower in the housing at 1 liter per minute flow rate.

11. The device of claim 1 wherein a condensation rate of the aerosol is less than 50% in the housing at 0.5 liters per minute flow rate.

12. The device of claim 1 wherein a condensation rate of the aerosol is less than 40% in the housing at 0.5 liters per minute flow rate.

13. The device of claim 1 wherein the nasal cannula is configured for use by a patient selected from the group consisting of micro preemie, preemie, newborn, and infant.

14. A non-transitory computer readable medium comprising storing computer readable instructions, configured to be acted upon by a 3D printer configured to cause the 3D printer to print an adaptor comprising:
a) a housing, wherein the housing includes a base and a cylindrical wall, wherein the base and the cylindrical wall define a chamber through which supplemental oxygen is led, and
b) two couplers, wherein a first of the two couplers is an inlet for supplemental oxygen supply into the chamber, wherein a second of the two couplers is an outlet for delivery of the supplemental oxygen supply containing an aerosol, wherein each of the two couplers is configured to engage a nasal cannula line,
wherein the cylindrical wall is configured to snugly fit to an aerosol delivery portion of a nebulizer, wherein the aerosol delivery portion of the nebulizer is not positioned to act as a baffle to air flow between the two couplers, wherein there is no baffle or impediment to air flow and aerosol through the adaptor,
wherein the housing and the couplers are designed to facilitate laminar flow, wherein the non-transitory computer readable medium is configured to cause the 3D printer to print an adaptor wherein a void starts in a slightly larger cylindrical portion and terminates in the chamber, wherein the void is shaped as an end of an ellipsoid and the void extends outward and perpendicular from the cylindrical wall.

15. A method for producing an adaptor for delivery of aerosol along with supplemental oxygen from an oxygen supply to a nasal cannula of a patient, the method comprising:
causing an additive printing device to print the adaptor according to a prescribed printing process having prescribed parameters; the adaptor comprising:
a housing, wherein the housing includes a base and a cylindrical wall, wherein the base and the cylindrical wall define a chamber through which supplemental oxygen is configured to be led, and
two couplers, wherein a first of the two couplers is an inlet for supplemental oxygen supply into the chamber, wherein a second of the two couplers is an outlet for delivery of the supplemental oxygen supply containing an aerosol, wherein each of the two couplers is configured to engage a nasal cannula line,
wherein the cylindrical wall is configured to snugly fit to an aerosol delivery portion of a nebulizer, wherein the aerosol delivery portion of wherein the aerosol delivery portion of the nebulizer is not positioned is not positioned to act as a baffle to air flow between the two couplers, wherein there is no baffle or impediment to air flow and aerosol through the adaptor,
wherein the housing and couplers are designed to facilitate laminar flow,
the housing, base, cylindrical wall, and couplers are integrally formed, and wherein each of the two couplers defines a void which is shaped as an end of an ellipsoid and the void extends outward and perpendicular from the cylindrical wall.

16. The method of claim 15, wherein causing an additive printing device to print the device comprises printing the device in a plurality of layers.

17. The method of claim 15 wherein the additive printing device comprises a 3D printer.

* * * * *